United States Patent
Itai

(10) Patent No.: US 9,119,599 B2
(45) Date of Patent: Sep. 1, 2015

(54) MEDICAL IMAGE DISPLAY APPARATUS, MEDICAL IMAGE DISPLAY METHOD AND NON-TRANSITORY COMPUTER-READABLE RECORDING MEDIUM HAVING STORED THEREIN MEDICAL IMAGE DISPLAY PROGRAM

(71) Applicant: FUJIFILM Corporation, Tokyo (JP)

(72) Inventor: Yoshinori Itai, Tokyo (JP)

(73) Assignee: Fujifilm Corporation, Tokyo (JP)

(*) Notice: Subject to any disclaimer, the term of this patent is extended or adjusted under 35 U.S.C. 154(b) by 0 days.

(21) Appl. No.: 14/476,487

(22) Filed: Sep. 3, 2014

(65) Prior Publication Data

US 2015/0002547 A1 Jan. 1, 2015

Related U.S. Application Data

(63) Continuation of application No. PCT/JP2013/001234, filed on Feb. 28, 2013.

(30) Foreign Application Priority Data

Mar. 5, 2012 (JP) ................................. 2012-047538

(51) Int. Cl.
*G09G 5/00* (2006.01)
*A61B 5/00* (2006.01)
(Continued)

(52) U.S. Cl.
CPC ................ *A61B 5/742* (2013.01); *A61B 6/463* (2013.01); *G06T 7/0014* (2013.01);
(Continued)

(58) Field of Classification Search
None
See application file for complete search history.

(56) References Cited

U.S. PATENT DOCUMENTS 8,374,410 B2  2/2013  Ohyu et al.
2006/0233430 A1  10/2006  Kimura
(Continued)

FOREIGN PATENT DOCUMENTS

JP  10-137231 A  5/1998
JP  2006-314778 A  11/2006
(Continued)

OTHER PUBLICATIONS

D. Mattes et al., "Nonrigid multimodality image registration", Proceedings of the SPIE, vol. 4322, pp. 1609-1620, 2001.
(Continued)

*Primary Examiner* — Kee M Tung
*Assistant Examiner* — Frank Chen
(74) *Attorney, Agent, or Firm* — McGinn IP Law Group, PLLC

(57) ABSTRACT

First tomographic-image information for identifying a first tomographic-image included in a first image and first region-of-interest information for identifying a first region of interest on the first tomographic-image are obtained. An image deformation amount of one of the first image and the second image for deforming the one of the first image and the second image to match the first image and the second image with each other is calculated. A slice image in the second image corresponding to the first tomographic-image is identified, based on image deformation amounts at plural positions in the first region of interest and the first tomographic-image information, as a second tomographic-image, and a region of interest in the second image corresponding to the first region of interest is identified, as a second region of interest. The first tomographic-image and the second tomographic-image onto which the second region of interest is projected are displayed.

8 Claims, 3 Drawing Sheets

(51) Int. Cl.
- *A61B 6/00* (2006.01)
- *G06T 7/00* (2006.01)
- *G06T 11/60* (2006.01)
- *A61B 6/03* (2006.01)

(52) U.S. Cl.
CPC .............. *G06T 7/0016* (2013.01); *G06T 11/60* (2013.01); *A61B 6/032* (2013.01); *A61B 6/037* (2013.01); *A61B 6/469* (2013.01); *A61B 6/5235* (2013.01); *G06T 2207/10072* (2013.01); *G06T 2207/20221* (2013.01); *G06T 2207/30004* (2013.01)

(56) References Cited

U.S. PATENT DOCUMENTS

2007/0280522 A1* 12/2007 Sugiyama ..................... 382/131
2008/0019580 A1    1/2008 Ohyu et al.
2012/0321195 A1* 12/2012 Jhunjhunwala et al. ...... 382/195

FOREIGN PATENT DOCUMENTS

| | | |
|---|---|---|
| JP | 2007-21193 A | 2/2007 |
| JP | 2008-43736 A | 2/2008 |
| JP | 2008-86400 A | 4/2008 |
| JP | 2009-522005 A | 6/2009 |
| JP | 2009-160045 A | 7/2009 |
| JP | 2009-195306 A | 9/2009 |
| JP | 2010-57532 A | 3/2010 |
| JP | 2011-24763 A | 2/2011 |
| JP | 2011-092677 A | 5/2011 |

OTHER PUBLICATIONS

International Search Report (ISR) (PCT Form PCT/ISA/210), in PCT/JP2013/001234, dated Jun. 4, 2013.

* cited by examiner

MEDICAL IMAGE DISPLAY APPARATUS, MEDICAL IMAGE DISPLAY METHOD AND NON-TRANSITORY COMPUTER-READABLE RECORDING MEDIUM HAVING STORED THEREIN MEDICAL IMAGE DISPLAY PROGRAM

CROSS-REFERENCE TO RELATED APPLICATIONS

This application is a Continuation of PCT International Application No. PCT/JP2013/001234 filed on Feb. 28, 2013, which claims priority under 35 U.S.C. §119(a) to Japanese Patent Application No. 2012-047538 filed on Mar. 5, 2012. Each of the above applications is hereby expressly incorporated by reference, in its entirety, into the present application.

BACKGROUND OF THE INVENTION

1. Field of the Invention

The present invention relates to a medical image display apparatus, a medical image display method and a medical image display program for displaying two images in such a manner that comparative image reading on regions of interest in the two images is possible when the two images have been obtained by imaging a same subject at different points in time.

2. Description of the Related Art

In image-based diagnosis using two three-dimensional images obtained by imaging a same subject at different points in time by using same or different imaging apparatuses (modalities), a non-rigid registration technique has been drawing attention. In the non-rigid registration technique, a transformation function that matches the spatial positions of the subject in the two images with each other when the two images are placed one on the other is estimated, and the positions of the two kinds of image are matched with each other by deforming one of the images by using the estimated transformation function. In this non-rigid registration technique, control points for dividing image space at predetermined intervals are set. Then, deformation amounts of the control points that maximize an evaluation function for evaluating the similarity of voxel values between one of the images that is deformed by displacing the positions of the control points and the other image are determined. The transformation function is estimated based on the deformation amount of the control point at this time.

Japanese Unexamined Patent Publication No. 2011-092677 (Patent Document 1), PCT Japanese Publication No. 2009-522005 (Patent Document 2) and Japanese Unexamined Patent Publication No. 2008-086400 (Patent Document 3) present medical image display methods in comparative display of medical images representing an organ at plural points in time. In the methods, a region of interest in a medical image at a point in time corresponding to a region of interest in a medical image at a different point in time is identified by using the non-rigid registration technique. Further, one of the medical images is deformed so that the medical images representing the organ at plural points in time match with each other. A medical image that represents a region of interest at a point in time and a medical image that corresponds to this medical image and represents a region of interest at a different point in time (an image deformed to match medical images representing the organ at different points in time with each other) are displayed in such a manner to be comparable with each other. Further, Japanese Unexamined Patent Publication No. 2009-195306 (Patent Document 4) presents a medical image display method in comparative display of medical images representing bronchi at plural points in time. In the method, a corresponding landmark (a branching region in the bronchi) is extracted from each of the medical images, and a coordinate transformation parameter for matching the corresponding landmarks with each other is calculated by using a linear optimization technique. A medical image representing a region of interest at a point in time and a medical image that corresponds to this medical image and represents a region of interest at a different point (an image generated by performing coordinate transformation using the coordinate transformation parameter) are displayed, based on the calculated coordinate transformation parameter, in such a manner to be comparable with each other.

SUMMARY OF THE INVENTION

Meanwhile, in a practice of observing the course of the condition of a patient at actual medical sites, corresponding tomographic images at different points in time are used in comparative image reading. There is a demand for performing comparative image reading by more precisely matching the positions of tomographic images at different points in time with each other, and also by displaying the tomographic images without deforming them so that the real shape of an organ, a region of interest and the like is accurately observable. Therefore, the methods disclosed in Patent Documents 1 through 4 need to identify, based on a transformation function or a coordinate transformation parameter for position matching, a tomographic image representing a region of interest at a more accurately corresponding position, and also to display the identified tomographic image for comparison without deforming the tomographic image.

In view of the foregoing circumstances, it is an object of the present invention to provide a medical image display apparatus, a medical image display method and a medical image display program that can display tomographic images for comparison at more accurately corresponding positions in such a manner to be comparable with each other when two images have been obtained by imaging a same subject at different points in time.

To achieve the aforementioned objects, a medical image display apparatus of the present invention includes an image obtainment unit that obtains a first image and a second image, which are three-dimensional images obtained by imaging a same patient at different points in time, a first tomographic image information obtainment unit that obtains first tomographic image information, which is information for identifying a first tomographic image that is a slice image included in the first image, and first region-of-interest information, which is information for identifying a first region of interest on the first tomographic image, a deformation amount calculation unit that calculates an image deformation amount of one of the first image and the second image for deforming the one of the first image and the second image to match the first image and the second image with each other, a second tomographic image identification unit that obtains, based on the calculated image deformation amount of the one of the first image and the second image and the first region-of-interest information, image deformation amounts at a plurality of positions included in a region of interest on the one of the first image and the second image, and identifies, based on the image deformation amounts at the plurality of positions and the first tomographic image information, a slice image in the second image corresponding to the first tomographic image, as a second tomographic image, and also identifies, based on the calculated image deformation amount of the one of the first image and the second image and the first region-ofinterest information, a region of interest in the second image corresponding to the first region of interest, as a second region of interest, and a display control unit that makes the first tomographic image and the identified second tomographic image displayed on a display device in such a manner to be comparable with each other, and also makes the identified second region of interest distinguishably displayed on the second tomographic image by projecting the second region of interest onto the second tomographic image.

Further, a medical image display method of the present invention is a medical image display method to be performed by a medical image display apparatus comprising an image obtainment unit, a first tomographic image information obtainment unit, a deformation amount calculation unit, a second tomographic image identification unit and a display control unit. The method includes an image obtainment step that obtains a first image and a second image, which are three-dimensional images obtained by imaging a same patient at different points in time, a first tomographic image information obtainment step that obtains first tomographic image information, which is information for identifying a first tomographic image that is a slice image included in the first image, and first region-of-interest information, which is information for identifying a first region of interest on the first tomographic image, a deformation amount calculation step that calculates an image deformation amount of one of the first image and the second image for deforming the one of the first image and the second image to match the first image and the second image with each other, a second tomographic image identification step that obtains, based on the calculated image deformation amount of the one of the first image and the second image and the first region-of-interest information, image deformation amounts at a plurality of positions included in a region of interest on the one of the first image and the second image, and identifies, based on the image deformation amounts at the plurality of positions and the first tomographic image information, a slice image in the second image corresponding to the first tomographic image, as a second tomographic image, and also identifies, based on the calculated image deformation amount of the one of the first image and the second image and the first region-of-interest information, a region of interest in the second image corresponding to the first region of interest, as a second region of interest, and a display control step that makes the first tomographic image and the identified second tomographic image displayed on a display device in such a manner to be comparable with each other, and also makes the identified second region of interest distinguishably displayed on the second tomographic image by projecting the second region of interest onto the second tomographic image.

A medical image display program of the present invention causes a computer to function as an image obtainment unit that obtains a first image and a second image, which are three-dimensional images obtained by imaging a same patient at different points in time, a first tomographic image information obtainment unit that obtains first tomographic image information, which is information for identifying a first tomographic image that is a slice image included in the first image, and first region-of-interest information, which is information for identifying a first region of interest on the first tomographic image, a deformation amount calculation unit that calculates an image deformation amount of one of the first image and the second image for deforming the one of the first image and the second image to match the first image and the second image with each other, a second tomographic image identification unit that obtains, based on the calculated image deformation amount of the one of the first image and the second image and the first region-of-interest information, image deformation amounts at a plurality of positions included in a region of interest on the one of the first image and the second image, and identifies, based on the deformation amounts at the plurality of positions and the first tomographic image information, a slice image in the second image corresponding to the first tomographic image, as a second tomographic image, and also identifies, based on the calculated image deformation amount of the one of the first image and the second image and the first region-of-interest information, a region of interest in the second image corresponding to the first region of interest, as a second region of interest, and a display control unit that makes the first tomographic image and the identified second tomographic image displayed on a display device in such a manner to be comparable with each other, and also makes the identified second region of interest distinguishably displayed on the second tomographic image by projecting the second region of interest onto the second tomographic image.

The first image and the second image in the present invention should be images representing a same subject, and which are obtained by imaging the subject at different timings. The first image and the second image may be imaged by using different modalities. However, it is desirable that the first image and the second image are imaged by using the same modalities to accurately perform comparative image reading. For example, CT, MRI, PET, SPECT, ultrasonic images and the like may be adopted as modalities of the present invention.

The "first tomographic image information" may be information for identifying a first tomographic image by using an arbitrary method that can identify the first tomographic image. For example, the first tomographic image information may be the series name of the first tomographic image, the coordinate or coordinates of at least one position on the first tomographic image, and information representing a normal vector of the first tomographic image. As another example, when the first image is a CT image and the first tomographic image is an axial (axial section) image, the series name and the slice number of the first tomographic image may be the first tomographic image information.

The "first region-of-interest information" may identify the first region of interest by using an arbitrary method that can identify the first region of interest.

In the medical image display apparatus of the present invention, the first region of interest may be defined by using an arbitrary method. For example, the first region of interest may be a predetermined polyhedral region defined based on plural positions on the boundary of the first region of interest. Further, the first region of interest may be identified based on two positions on the boundary of the first region of interest facing each other with the first region of interest therebetween. For example, the polyhedral region may be a sphere, a rectangular parallelepiped, or the like. Further, the first region of interest may be composed of an arbitrary curved surface.

Further, in the medical image display apparatus of the present invention, it is desirable that the second tomographic image identification unit identifies the second tomographic image in such a manner that an angle between the second tomographic image and a body axis of the patient and an angle between the first tomographic image and the body axis of the patient are equal, and also that the second tomographic image includes at least one position to which at least one position in the second image that has the same coordinate or coordinates as the coordinate or coordinates of at least one point in the first tomographic image is moved by a mean value or a median value of image deformation amounts at a plurality of positions included in the first region of interest.

Further, it is desirable that the first region-of-interest information represents a plurality of positions on a boundary of the first region of interest, and that the second tomographic image identification unit calculates an image deformation amount of the first region of interest by obtaining a weighted average of image deformation amounts corresponding to positions included in the first region of interest by increasing weighting as distances from the plurality of positions on the boundary of the first region of interest to each of the positions included in the first region of interest are shorter.

In the medical image display apparatus of the present invention, it is desirable that the display control unit projects only an outline of the second region of interest onto the second tomographic image, and distinguishably displays an index of the projected outline on the second tomographic image.

According to the present invention, an image obtainment unit that obtains a first image and a second image, which are three-dimensional images obtained by imaging a same patient at different points in time, a first tomographic image information obtainment unit that obtains first tomographic image information, which is information for identifying a first tomographic image that is a slice image included in the first image, and first region-of-interest information, which is information for identifying a first region of interest on the first tomographic image, a deformation amount calculation unit that calculates an image deformation amount of one of the first image and the second image for deforming the one of the first image and the second image to match the first image and the second image with each other, a second tomographic image identification unit that obtains, based on the calculated image deformation amount of the one of the first image and the second image and the first region-of-interest information, image deformation amounts at a plurality of positions included in a region of interest on the one of the first image and the second image, and identifies, based on the image deformation amounts at the plurality of positions and the first tomographic image information, a slice image in the second image corresponding to the first tomographic image, as a second tomographic image, and also identifies, based on the calculated image deformation amount of the one of the first image and the second image and the first region-of-interest information, a region of interest in the second image corresponding to the first region of interest, as a second region of interest, and a display control unit that makes the first tomographic image and the identified second tomographic image displayed on a display device in such a manner to be comparable with each other, and also makes the identified second region of interest distinguishably displayed on the second tomographic image by projecting the second region of interest onto the second tomographic image are provided. When the course of the condition of a patient is observed, a lesion or the like, which spreads to some extent, is often used as a region of interest. Therefore, when the position of the second tomographic image is identified by using information about deformation amounts at plural positions in the first region of interest, it is possible to appropriately identify the position of the second tomographic image corresponding to the first tomographic image, and to display the images to be comparable with each other. Hence, it is possible to assist accurate comparative image reading.

DESCRIPTION OF THE PREFERRED EMBODIMENTS

Hereinafter, embodiments of a medical image display apparatus, a medical image display program and a medical image display method of the present invention will be described in detail with reference to drawings.

Figure 1:
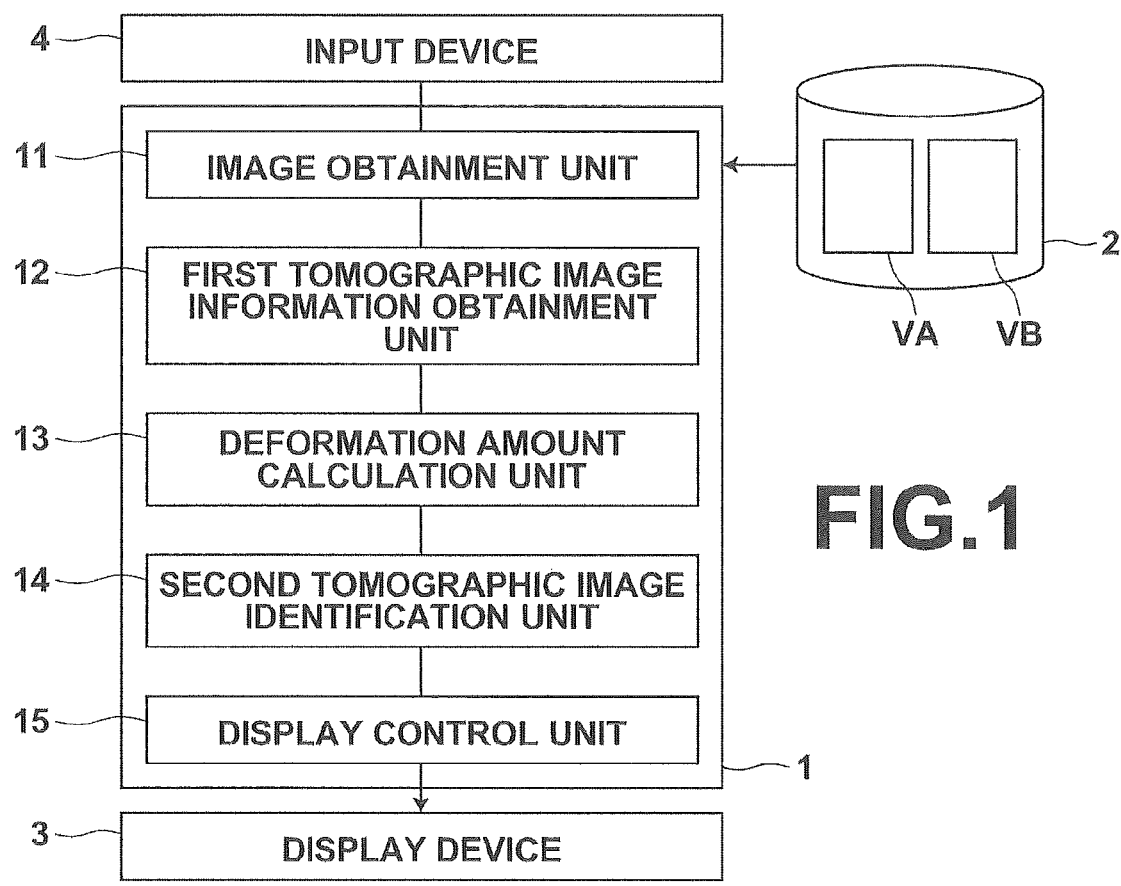
FIG. 1 is a schematic electrical block diagram of a medical image display apparatus according to an embodiment of the present invention.

FIG. 1 is a schematic diagram illustrating the configuration of a medical image display apparatus realized by installing a medical image display program in a workstation used by a doctor. A medical image display apparatus 1 includes, as the configuration of a standard workstation, a processor and a memory (both of which are not illustrated). Further, the medical image display apparatus 1 includes a storage 2, such as an HDD (Hard Disk Drive). Further, a display 3 and an input device 4, such as a mouse and a keyboard, are connected to the medical image display apparatus 1.

The medical image display program and data referred to by the medical image display program are stored in the storage 2 at the time of installation, and loaded into the memory at boot-up. The medical image display program defines, as processing performed by a CPU, image obtainment processing, first tomographic image information obtainment processing, deformation amount calculation processing, second tomographic image identification processing and display control processing.

When the CPU executes each of the aforementioned kinds of processing based on what is defined in the program, a general-purpose workstation functions as an image obtainment unit 11, a first tomographic image information obtainment unit 12, a deformation amount calculation unit 13, a second tomographic image identification unit 14 and a display control unit 15, as will be described later.

The storage 2 stores first image VA and second image VB transferred from an examination department in charge of imaging, or first image VA and second image VB retrieved from a database. In an embodiment of the present invention, first image VA and second image VB were obtained by imaging a same patient at first imaging time and at second imaging time, which was after the first imaging time, by a CT apparatus. Each of first image VA and second image VB was transferred from the examination department, and stored in the storage 2 to observe the course of the condition of the abdomen of a patient. Both of images VA, VB were obtained by imaging the same patient with the same posture to perform comparative image reading for analysis of a result of drug administration. It is assumed that the body axis of the patient and the direction of the body are substantially the same in the spatial coordinate systems of the two images. Further, it is assumed that processing for unifying the scales of both of images VA, VB has been performed on one of images VA, VB based on pixel size (Pixel Spacing) and slice interval (Slice Spacing) obtained from arbitrary information, such as header information of both of images VA, VB, by using a known method.

The image obtainment 11 obtains first image VA and second image VB from storage 2. In the embodiment of the present invention, when the medical image display apparatus 1 detects selection of a predetermined comparative display function in a selection menu, the medical image display apparatus 1 prompts a user to select or input information necessary to identify the first and second images. When the first image and the second image are identified by an operation by the user at the input device 4, the image obtainment unit 11 loads first image VA and second image VB from the storage 2 into the memory.

Figure 2A:
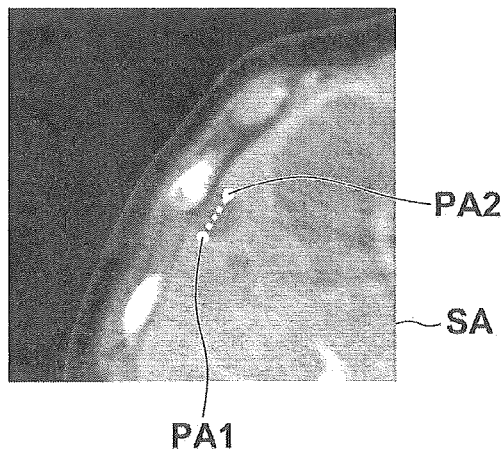
FIG. 2A is a diagram for explaining a method for inputting a region of interest on a first tomographic image in an embodiment of the present invention.
Figure 2B:
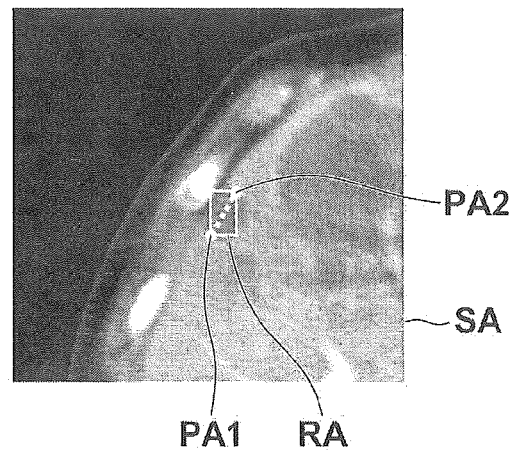
FIG. 2B is a diagram for explaining a method for obtaining a region of interest on the first tomographic image in an embodiment of the present invention.

The first tomographic image information obtainment unit 12 obtains first tomographic image information, which identifies first tomographic image SA that is a slice image included in first image VA, and first region-of-interest information, which identifies a first region of interest on the first tomographic image. FIG. 2A and FIG. 2B are diagrams of images for explaining a method for obtaining region-of-interest information. Both of the diagrams illustrate the same first tomographic image SA. First tomographic image SA represents xy cross section of first image VA, and is an axial image of the patient. Here, a radiologist in charge of image reading sequentially displays tomographic images (axial images) included in first image VA, and determines an observation image representing a region of interest, as first tomographic image SA, by selection by a predetermined selection button, or the like. Then, the first tomographic image information obtainment unit 12 obtains the series name and the slice number of the first tomographic image, as information for identifying first tomographic image SA (first tomographic image information), and stores the information in the memory.

Next, as illustrated in FIG. 2A, the first tomographic image information obtainment unit 12 receives an input of the positions of two pixels PA1, PA2 on the boundary of first region of interest RA, such as an abnormal shadow region, on first tomographic image SA by an input operation by the user at the input device 4, and pixels PA1, PA2 face each other with the first region of interest therebetween. Accordingly, the first tomographic image information obtainment unit 12 obtains the coordinates of pixels PA1, PA2, which have been input at the input device 4. Further, as illustrated in FIG. 2B, the first tomographic image information obtainment unit obtains the first region of interest, as a rectangular parallelepiped region identified based on the obtained positions of pixels PA1, PA2. Specifically, a rectangular parallelepiped having an upper surface that is a rectangle obtained by translation of a rectangle having a line connecting pixels PA1, PA2, as its diagonal line, in the direction of a normal to the first tomographic image (in a positive direction of z axis, which is toward the front side of FIG. 2B) by a predetermined length and a lower surface that is a rectangle obtained by translation of a rectangle having a line connecting pixels PA1, PA2, as its diagonal line, in the direction of a normal to the first tomographic image (in a negative direction of z axis, which is toward the back side of FIG. 2B) by a predetermined length, is identified as first region of interest RA. Here, it is assumed that the length of each side of the rectangles defined by the diagonal lines and the predetermined lengths of the rectangular parallelepiped in the z direction have been calculated in advance at predetermined ratios based on the lengths of the diagonal lines. Further, the first tomographic image information obtainment unit 12 obtains the coordinate of each vertex of a rectangular parallelepiped region that is first region of interest RA and information about the obtained coordinates of pixels PA1, PA2, as first region-of-interest identification information.

The deformation amount calculation unit 13 deforms first image VA, and evaluates a degree of similarity between deformed first image VA and second image VB by using an evaluation function representing the degree of similarity between pixel values of deformed first image VA and corresponding pixel values of second image VB. Further, the deformation amount calculation unit 13 calculates a deformation amount (image deformation amount) of the first image to match the deformed first image and the second image match with each other.

Here, first, the deformation amount calculation unit 13 sets set X composed of control points x1, x2, ... xn, which divide image space at predetermined intervals, in each of first image VA and second image VB. Hereinafter, the set of control points x1, x2, ... xn will be referred to as control point X. The deformation amount calculation unit 13 deforms first image VA by displacing control point X in first image VA by deformation amount $\mu$ by known transformation function g. Control points to which control point X in first image VA is displaced by deformation amount $\mu$ by transformation function g will be referred to as $g(X,\mu)$. Further, an image obtained by deforming first image VA by displacing control point X in first image VA by deformation amount $\mu$ by transformation function g will be referred to as deformed first image VA'.

Next, the deformation amount calculation unit 13 obtains pixel value $M(g(X,\mu))$ at control point $g(X,\mu)$ in deformed first image VA'. Further, the deformation amount calculation unit 13 obtains pixel value $F(X)$ at control point X in second image VB. The deformation amount calculation unit 13 determines deformation amount $\mu$ of control point X when an evaluation function (registration function) representing the degree of similarity between pixel value $M(g(X,\mu))$ at each control point $g(X,\mu)$ in deformed first image VA' and pixel value $F(X)$ at each control point X in second image VB is maximized. The deformation amount calculation unit 13 estimates a transformation function for first image VA based on deformation amount $\mu$ of control point X of this time. In the evaluation function in the embodiment of the present invention, it is assumed that an evaluation value is larger as the degree of similarity is higher.

The deformation amount calculation unit 13 may use a known non-rigid registration technique to calculate a deformation amount of the first image to match a subject in the first image and the subject in the second image with each other, and to estimate a transformation function based on the deformation amount. Here, it is assumed that a non-rigid registration technique described in D. Mattes et al., "Nonrigid multimodality image registration", Proceedings of the SPIE, Vol. 4322, pp. 1609-1620, 2001 is used.

Next, the second tomographic image identification unit 14 identifies, based on image deformation amounts at plural positions included in first region of interest RA among the calculated image deformation amounts and first tomographic image information, a slice image in second image VB corresponding to first tomographic image SA, as second tomographic image SB. Further, the second tomographic image identification unit 14 identifies a region of interest in second image VB corresponding to first region of interest RA, as second region of interest RB.

Specifically, first, the second tomographic image identification unit 14 transforms first image VA by the transformation function estimated by the deformation amount calculation unit 13, and identifies corresponding pixels between first image VA and second image VB. Then, the second tomographic image identification unit 14 calculates, based on the first region-of-interest information, a deformation amount at each position in first region of interest RA to deform first image VA to match first image VA with second image VB. Next, the second tomographic image identification unit 14 obtains average value T (Tx, Ty, Tz) of deformation amounts at all pixels included in the first region of interest with respect to each of x, y and z directions in the three-dimensional coordinate system of first image VA.

Figure 3:
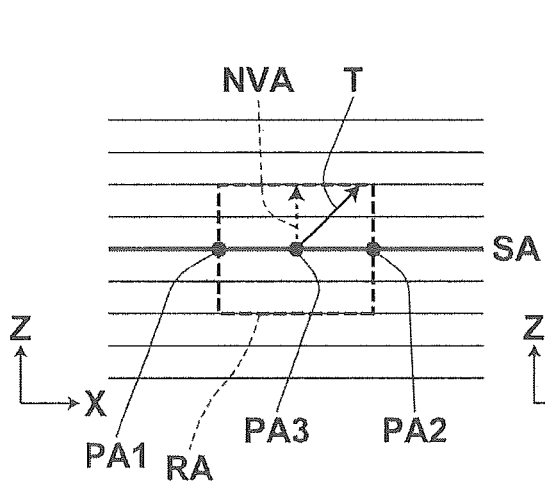
FIG. 3 is a diagram for explaining a method for identifying a second tomographic image in an embodiment of the present invention.
Figure 3:
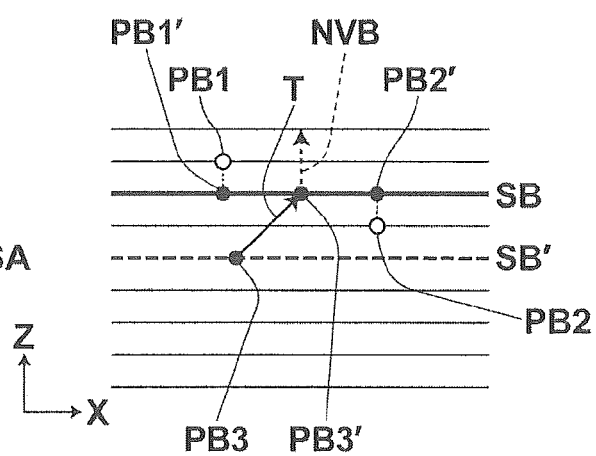

FIG. 3 is a diagram for explaining a method for identifying a second tomographic image. The left-side section of FIG. 3 is a diagram illustrating xz cross section of first image VA, and which shows first image VA in a direction perpendicular to FIGS. 2A, 2B. In the left-side section of FIG. 3, tomographic images constituting first image VA are indicated by horizontal lines, and first tomographic image SA is indicated by a bold horizontal line. The right-side section of FIG. 3 is a diagram illustrating xz cross section of second image VB. In the right-side section of FIG. 3, plural tomographic images constituting second image VB are indicated by horizontal lines, and second tomographic image SB is indicated by a bold horizontal line.

The second tomographic image identification unit 14 calculates the coordinate of pixel PA3, which is located at a middle point between PA1 and PA2 on first tomographic image SA. Further, the second tomographic image identification unit 14 obtains the coordinate of PB3', to which the position of pixel PB3 in second image VB having the same coordinate as PA3 is moved by average value T of deformation amounts of all pixels in first region of interest. Then, the second tomographic image identification unit 14 identifies an axial image including PB3' in second image VB, as second tomographic image SB. Here, both of first tomographic image SA and second tomographic image SB are axial images (slice images representing a patient in a predetermined direction). Therefore, an angle between normal vector NVA (an arrow indicated by a broken line in the left-side section of FIG. 3) of first tomographic image SA and the body axis of the patient and an angle between normal vector NVB (an arrow indicated by a broken line in the right-side section of FIG. 3) of second tomographic image SB and the body axis of the patient are equal.

Here, when no axial image including PB3' is present in second image VB because of setting of slice intervals, an axial image including PB3' in second image VB is generated by interpolating an axial image between two axial images next to each other in z direction with PB3' therebetween, and this generated image is used as second tomographic image SB. Further, when the posture and the direction of a subject are same in first image VA and second image VB as in the embodiment of the present invention, with respect to a plane including first tomographic image SA in the coordinate system of first image VB, a plane located at the same position as the plane including first tomographic image SA may be identified in the coordinate system in second image VB. Further, a plane obtained by moving this identified plane in the direction of z by average value Tz of movement amounts in z direction may be used as second tomographic image SB.

The second tomographic image identification unit 14 identifies a region composed of pixels in second image VB corresponding to all pixels included in first region of interest RA, as second region-of-interest region RB. Further, the second tomographic image identification unit calculates coordinates on second tomographic image onto which the coordinates of pixels located on the outline of second region of interest RB are projected perpendicularly. PB1 and PB2 in second image VB, illustrated in the right-side section of FIG. 3, are pixels corresponding to PA1 and PA2 in first tomographic image SA, respectively. In this example, PA1 and PA2 are included in first tomographic image SA in first image VA. However, both of PB1 and PB2 are located at positions that are not included in second tomographic image SB because of temporal change, a slight difference in the posture of the patient during imaging or the like. For comparative observation, it is desirable to indicate where pixels PA1, PA2 facing each other with first region of interest RA therebetween, and which have been specified by an operation by the user, are located on second tomographic image SB. Therefore, in the embodiment of the present invention, the outline of first region of interest RA is projected onto second tomographic image SB, and displayed. Therefore, as illustrated in the right-side section of FIG. 3, the coordinates of PB1', PB2' on second tomographic image SB onto which pixels PB1, PB2 corresponding to pixels PA1, PA2 on the outline of first region of interest RA are projected are obtained.

The display control unit 15 makes first tomographic image SA and second tomographic image SB displayed on display 3 in such a manner to be comparable with each other. Further, the display control unit 15 projects second region of interest RB onto second tomographic image SB, and makes second region of interest RB distinguishably displayed. Here, the display control unit 15 may make obtained first image VA and second image VB and/or each image generated during execution of the medical image display program according to the embodiment of the present invention on the display 3, if necessary for an input by a user, or the like.

Figure 4:
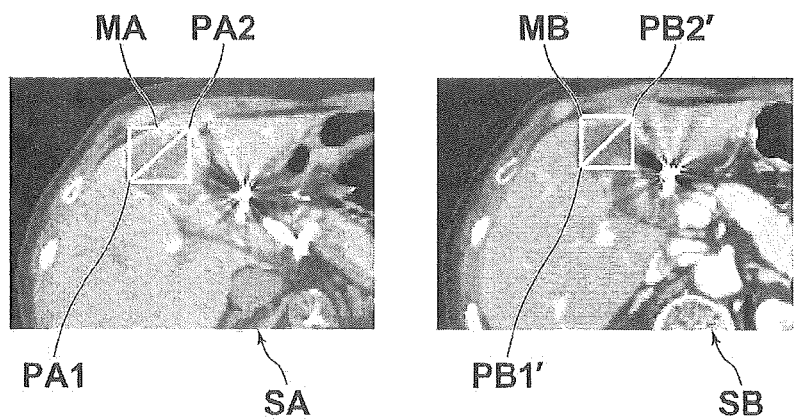
FIG. 4 is a diagram illustrating an example of display of a first tomographic image and a second tomographic image in an embodiment of the present invention.

FIG. 4 is a diagram illustrating an example of comparative display of first tomographic image SA and second tomographic image SB. As illustrated in FIG. 4, in the embodiment of the present invention, the display control unit 15 distinguishably displays the outline of second region of interest RB projected onto second tomographic image SB by using white index MA. In the embodiment of the present invention, the display control unit 15 distinguishably displays first region of interest RA and two pixels PA1, PA2, which have been specified on the boundary of first region of interest RA by an operation by a user, on first tomographic image SA. Further, the display control unit 15 distinguishably displays pixels PB1', PB2' at positions on second tomographic image SB onto which the positions of pixels PB1, PB2 corresponding to two pixels PA1, PA2 are projected.

Figure 5:
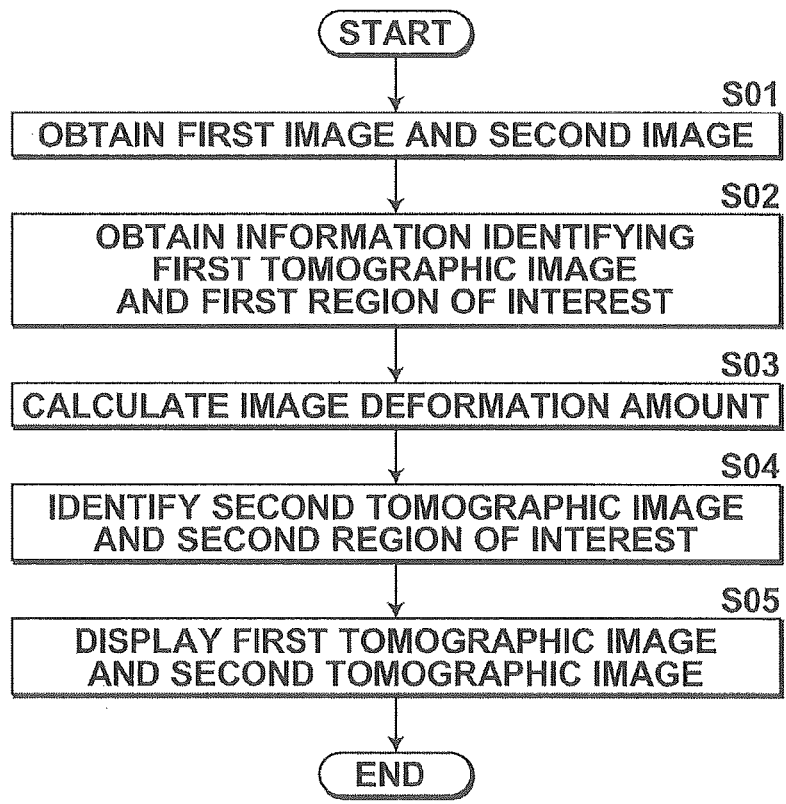
FIG. 5 is a flow chart illustrating the operation of a medical image display apparatus according to an embodiment of the present invention.

FIG. 5 is a flow chart illustrating a desirable embodiment of a medical image display method of the present invention. Medical image display according to embodiments of the present invention will be described with reference to FIG. 5.

First, the image obtainment unit 11 obtains first image (first image data) VA and second image (second image data) VB obtained by imaging a subject (S01). Next, the first tomographic image information obtainment unit 12 obtains information for identifying first tomographic image SA and information for identifying first region of interest RA included in first tomographic image SA (S02) Then, the deformation amount calculation unit 13 calculates deformation amount μ to maximize the evaluation function based on the evaluation function representing the degree of similarity between pixel values of first image VA and pixel values of second image VB. Further, the deformation amount calculation unit 13 estimates, based on the calculated deformation amount, a transformation function to match the pixel values of first image VA and the pixel values of second image VB with each other (S03).

Then, the second tomographic image identification unit 14 identifies, based on image deformations amounts at plural positions in first region of interest RA, second tomographic image SB and second region of interest RB (S04). Then, as illustrated in FIG. 4, the display control unit 15 displays first tomographic image SA and second tomographic image SB next to each other in such a manner to be comparable with each other. Further, the display control unit distinguishably displays a region of interest on second tomographic image SB by using index MB of an outline (S05).

According to the embodiment of the present invention, the second tomographic image identification unit identifies, based on deformation amounts at plural positions included in first region of interest RA, corresponding second tomographic image SB. When the course of the condition of a patient is observed, a lesion or the like, which spreads to some extent, is often used as a region of interest. Therefore, when the position of the second tomographic image is identified by using information about deformation amounts at plural positions in the first region of interest, it is possible to appropriately identify the position of the second tomographic image SB corresponding to the first tomographic image SA by using the deformation amounts at plural positions in the first region of interest for judgment, and to display the images for comparison. Consequently, it is possible to assist accurate comparative image reading. In the above embodiment, corresponding second tomographic image SB was identified based on deformation amounts at all positions included in first region of interest RA. Therefore, the aforementioned effects are more remarkably achievable. However, the present invention is not limited to the embodiment of the present invention. Corresponding second tomographic image SB may be identified based on a deformation amount or amounts at a part of positions included in first region of interest RA.

Further, according to the methods disclosed in Patent Documents 1 through 4, a deformed image of one of images is generated, and displayed. However, according to the embodiments of the present invention, tomographic images at corresponding positions at two points in time, and which are not deformed, are displayed in such a manner to be comparable to observe the course of the condition of a patient. Therefore, it is possible to display a tomographic image satisfying a demand for performing comparative image reading by displaying the tomographic image without deforming the tomographic image so as to accurately observe the real shape of an organ and a region of interest in the practice of diagnosis. Further, it is possible to save the cost of processing for generating a deformed image, which is required in the methods disclosed in Patent Documents 1 through 4.

According to the embodiment of the present invention, the second tomographic image identification unit 14 identifies second tomographic image in such a manner that an angle between second tomographic image SB and a body axis of the patient and an angle between first tomographic image SA and the body axis of the patient are equal, and also that the second tomographic image includes at least one position to which at least one position in the second image that has the same coordinate or coordinates as the coordinate or coordinates of at least one point in the first tomographic image is moved by a mean value of image deformation amounts at plural positions included in the first region of interest. Therefore, the inclination of a slice plane represented by the first tomographic image and the inclination of a slice plane represented by the second tomographic image appropriately correspond to each other. Here, also when a median value of image deformation amounts at plural positions included in the first region of interest is used instead of the mean value of image deformation amounts at plural positions included in the first region of interest, the same effect is achievable. In the first embodiment, the first tomographic image and the second tomographic image are axial images used in the current practice of observation of the course of the condition of a patient. Therefore, those in medical fields can easily observe the images, and it is possible to effectively improve the efficiency in image reading. Further, the second tomographic image identification unit 14 may identify the second tomographic image by using any method as long as the second tomographic image is identified in such a manner that an angle between second tomographic image SB and a body axis of the patient and an angle between first tomographic image SA and the body axis of the patient are equal, and also that the second tomographic image includes at least one position to which at least one position in the second image that has the same coordinate or coordinates as the coordinate or coordinates of at least one point in the first tomographic image is moved by an average value of image deformation amounts at plural positions included in the first region of interest.

In the embodiment of the present invention, the position of pixel PA3 located at a middle point between positions PA1, PA2 in the first tomographic image, which have been specified by the user, is associated with the position of pixel PB3' on second tomographic image SB, and second tomographic image SB is identified based on this PB3'. However, the present invention is not limited to this embodiment. A pair of a position in the first tomographic image and a position corresponding to this position in the second tomographic image may be arbitrarily determined. When a position in the first tomographic image corresponding to a position included in the second tomographic image is a position in the first region of interest, the second tomographic image appropriately includes a position in the region of interest. Therefore, that is desirable to observe the region of interest on the second tomographic image. In this respect, as in the embodiment of the present invention, when the center (or the center of gravity) of the first region of interest corresponds to a position on the second tomographic image, it is possible to make the second tomographic image include a position corresponding to the center (or the center of gravity) of the first region of interest. Therefore, the second tomographic image is highly likely to more appropriately represent the region of interest.

Further, according to the embodiment of the present invention, second tomographic image SB and the second region of interest are displayed for comparison only by specifying the region of interest in one of the images. Therefore, it is possible to reduce the burden on the user in operations, compared with a conventional case in which tomographic images for comparative image reading are extracted from first and second image VA, VB by manual operations by the user, and corresponding regions of interest are set on the extracted tomographic images also by manual operations by the user.

Further, since first region of interest RA is a rectangular parallelepiped region, which is a predetermined polyhedral region, defined based on the positions of plural pixels PA1, PA2 on the boundary of the first region of interest. Therefore, an operation for inputting the first region of interest by the user is easy. Further, a polyhedral region in arbitrary shape, such as a sphere and a cube, may be adopted as the predetermined polyhedral region. Further, an arbitrary method may be used as a method for specifying the predetermined polyhedral region by the operations by the user.

Further, since first region of interest RA is identified based on the positions of two pixels PA1, PA2 on the boundary of the first region of interest facing each other with the first region of interest therebetween, the operation of inputting the first region of interest by the user is easy.

The present invention is not limited to the embodiment of the present invention. The first region of interest may be a two-dimensional region on the first tomographic image. Further, the first region of interest may be composed of a curved surface. Alternatively, the first region of interest may be composed of a combination of a curved surface and a flat surface. Further, the first region of interest may be a region obtained by recognizing the region by using a known image recognition technique instead of the region obtained by receiving an operation by the user at the input device.

Further, since the display control unit 15 projects only the outline of second region of interest RB onto second tomographic image SB, and distinguishably displays index MB of the projected outline on second tomographic image SB, it is possible to easily recognize second region of interest SB. Further, when the user measures the region of interest, such as a lesion, on the second tomographic image, the user can use the size of the displayed index to obtain information usable as a guide for measurement. For example, the user may use the size of the rectangular index in the embodiment of the present invention, as a target of the size of the region of interest. Alternatively, the user may use the length of a diagonal line connecting PA1 and PA2 in the rectangular index in the embodiment of the present invention, as the target of the diameter of the region of interest. Second region of interest RB may be displayed by using a known method as long as second region of interest RB is projected onto second tomographic image SB, and distinguishably displayed. For example, a projection image of second region of interest RB may be displayed as a semitransparent image. Further, as in the embodiment of the present invention, when the outline of second region of interest RB is projected onto second tomographic image SB and distinguishably displayed, and the outline of first region of interest RA is also displayed on first tomographic image SA, it is possible to easily compare the regions of interest with each other. Therefore, it is possible to improve the efficiency of image reading.

In the embodiment of the present invention, the positions of two pixels PA1, PA2 specified on the boundary of the region of interest by an operation by the user, and which face each other with the region of interest therebetween, are displayed on first tomographic image SA. Further, pixels PB1', PB2' on second tomographic image SB, onto which PA1, PA2 are projected, and which are at positions corresponding to PA1, PA2, are displayed on second tomographic image SB. Therefore, comparison between the regions of interest is easier.

Further, as a modified example of the first embodiment, first region-of-interest information may be information representing plural positions on the boundary of the first region of interest. The second tomographic image identification unit 14 may calculate the image deformation amount of the first region of interest by obtaining a weighted average of image deformation amounts corresponding to positions included in the first region of interest by increasing weighting as distances from the plural positions on the boundary of the first region of interest to each of the positions are shorter. When the plural positions on the boundary are positions specified by operations by the user, the movement amount (a weighted average of deformation amounts) of the second tomographic image with respect to the first tomographic image may be calculated, based on the position of a region that has been discriminated as a region of interest by the user and deformation amounts in the vicinity of this position, by using the weighted average of deformation amounts obtained by increasing weighting on deformation amounts on the boundary of the region of interest. Therefore, it is possible to appropriately identify and display the second tomographic image located at a position corresponding to the user's region of interest and a deformation amount of the discriminated position.

Further, corresponding pixels between first image VA and second image VB may be determined by estimating a transformation function of first image VA based on the image deformation amount for deforming first image VA to match first image VA and second image VB with each other, and by transforming first image VA by using the estimated transformation function. Alternatively, corresponding pixels between first image VA and second image VB may be determined by estimating a transformation function of second image VB based on the image deformation amount for deforming second image VB to match first image VA and second image VB with each other, and by transforming second image VB by using the estimated transformation function. Further, a known non-rigid registration technique may be adopted as a non-rigid registration technique for matching first image VA and second image VB with each other.

In the embodiment of the present invention, either deformation amount calculation processing or first region-of-interest obtainment processing may be performed first, or they may be performed at the same time.

Each of the aforementioned embodiments is only as an example. None of the above explanations should be used to construe the technical field of the present invention in a limited manner.

Further, the system configuration, the hardware configuration, the flow of processing, the module configuration, user interface, the specific contents of processing and the like may be modified in various manners without departing from the spirit of the present invention, and such modifications are still within the technical scope of the present invention.

Further, the medical image display apparatus 1 may be configured by making plural computers share functions as means. As apparatuses constituting the system, such as the input device and display, any known apparatus may be adopted.

What is claimed is:

1. A medical image display apparatus comprising:
   an image obtainment unit that obtains a first image and a second image, which are three-dimensional images obtained by imaging a same patient at different points in time;
   a first tomographic image information obtainment unit that obtains first tomographic image information, which is information for identifying a first tomographic image that is a slice image included in the first image, and first region-of-interest information, which is information for identifying a first region of interest on the first tomographic image;
   a deformation amount calculation unit that calculates an image deformation amount of one of the first image and the second image for deforming the one of the first image and the second image to match the first image and the second image with each other;
   a second tomographic image identification unit that obtains, based on the calculated image deformation amount of the one of the first image and the second image and the first region-of-interest information, image deformation amounts at a plurality of positions included in a region of interest on the one of the first image and the second image, and identifies, based on the image deformation amounts at the plurality of positions and the first tomographic image information, a slice image in the second image corresponding to the first tomographic image, as a second tomographic image, and also identifies, based on the calculated image deformation amount of the one of the first image and the second image and the first region-of-interest information, a region of interest in the second image corresponding to the first region of interest, as a second region of interest; and
- a display control unit that makes the first tomographic image and the identified second tomographic image displayed on a display device in such a manner to be comparable with each other, and also makes the identified second region of interest distinguishably displayed on the second tomographic image by projecting the second region of interest onto the second tomographic image.

2. The medical image display apparatus, as defined in claim 1, wherein the second tomographic image identification unit identifies the second tomographic image in such a manner that an angle between the second tomographic image and a body axis of the patient and an angle between the first tomographic image and the body axis of the patient are equal, and also that the second tomographic image includes at least one position to which at least one position in the second image that has the same coordinate or coordinates as the coordinate or coordinates of at least one position in the first tomographic image is moved by a mean value or a median value of image deformation amounts at a plurality of positions included in the first region of interest.

3. The medical image display apparatus, as defined in claim 2, wherein the first region-of-interest information represents a plurality of positions on a boundary of the first region of interest, and
  wherein the second tomographic image identification unit calculates an image deformation amount of the first region of interest by obtaining a weighted average of image deformation amounts corresponding to positions included in the first region of interest by increasing weighting as distances from the plurality of positions on the boundary of the first region of interest to each of the positions included in the first region of interest are shorter.

4. The medical image display apparatus, as defined in claim 3, wherein the first region of interest is a predetermined polyhedral region defined based on the plurality of positions on the boundary of the first region of interest.

5. The medical image display apparatus, as defined in claim 4, wherein the first region of interest is identified based on two positions on the boundary of the first region of interest facing each other with the first region of interest therebetween.

6. The medical image display apparatus, as defined in claim 1, wherein the display control unit projects only an outline of the second region of interest onto the second tomographic image, and distinguishably displays an index of the projected outline on the second tomographic image.

7. A medical image display method to be performed by a medical image display apparatus comprising an image obtainment unit, a first tomographic image information obtainment unit, a deformation amount calculation unit, a second tomographic image identification unit and a display control unit, the method comprising:
  an image obtainment step that obtains a first image and a second image, which are three-dimensional images obtained by imaging a same patient at different points in time;
  a first tomographic image information obtainment step that obtains first tomographic image information, which is information for identifying a first tomographic image that is a slice image included in the first image, and first region-of-interest information, which is information for identifying a first region of interest on the first tomographic image;
  a deformation amount calculation step that calculates an image deformation amount of one of the first image and the second image for deforming the one of the first image and the second image to match the first image and the second image with each other;
  a second tomographic image identification step that obtains, based on the calculated image deformation amount of the one of the first image and the second image and the first region-of-interest information, image deformation amounts at a plurality of positions included in a region of interest on the one of the first image and the second image, and identifies, based on the image deformation amounts at the plurality of positions and the first tomographic image information, a slice image in the second image corresponding to the first tomographic image, as a second tomographic image, and also identifies, based on the calculated image deformation amount of the one of the first image and the second image and the first region-of-interest information, a region of interest in the second image corresponding to the first region of interest, as a second region of interest; and
  a display control step that makes the first tomographic image and the identified second tomographic image displayed on a display device in such a manner to be comparable with each other, and also makes the identified second region of interest distinguishably displayed on the second tomographic image by projecting the second region of interest onto the second tomographic image.

8. A non-transitory computer-readable recording medium having stored therein a medical image display program for causing a computer to function as:
  an image obtainment unit that obtains a first image and a second image, which are three-dimensional images obtained by imaging a same patient at different points in time;
  a first tomographic image information obtainment unit that obtains first tomographic image information, which is information for identifying a first tomographic image that is a slice image included in the first image, and first region-of-interest information, which is information for identifying a first region of interest on the first tomographic image;
  a deformation amount calculation unit that calculates an image deformation amount of one of the first image and the second image for deforming the one of the first image and the second image to match the first image and the second image with each other;
  a second tomographic image identification unit that obtains, based on the calculated image deformation amount of the one of the first image and the second image and the first region-of-interest information, image deformation amounts at a plurality of positions included in a region of interest on the one of the first image and the second image, and identifies, based on the image deformation amounts at the plurality of positions and the first tomographic image information, a slice image in the second image corresponding to the first tomographic image, as a second tomographic image, and also identifies, based on the calculated image deformation amount of the one of the first image and the second image and the first region-of-interest information, a region of interest in the second image corresponding to the first region of interest, as a second region of interest; and a display control unit that makes the first tomographic image and the identified second tomographic image displayed on a display device in such a manner to be comparable with each other, and also makes the identified second region of interest distinguishably displayed on the second tomographic image by projecting the second region of interest onto the second tomographic image.

\* \* \* \* \*